United States Patent [19]

Dingwall et al.

[11] 4,147,780

[45] Apr. 3, 1979

[54] ALPHA AMINOPHOSPHONOUS ACIDS FOR INHIBITING BACTERIA AND YEAST

[75] Inventors: John G. Dingwall, Sale; Eric K. Baylis, Stockport, both of England; Colin D. Campbell, Beith, Scotland

[73] Assignee: Ciba-Geigy Corporation, Ardsley, N.Y.

[21] Appl. No.: 799,428

[22] Filed: May 23, 1977
(Under 47 CFR 1.47)

[30] Foreign Application Priority Data

May 21, 1976 [GB] United Kingdom ............... 21000/76

[51] Int. Cl.$^2$ ..................... C07F 9/48; A61K 31/66

[52] U.S. Cl. .................. 424/211; 260/319.1; 260/332.5; 260/729 P; 260/332.3 R; 260/502.5; 424/200; 424/202; 546/22; 542/424; 542/425; 542/414

[58] Field of Search .................. 260/502.5; 424/211

[56] References Cited

U.S. PATENT DOCUMENTS

| | | | |
|---|---|---|---|
| 3,160,632 | 12/1964 | Toy et al. | 260/502.5 |
| 3,424,788 | 1/1969 | Guttmann et al. | 260/502.5 |

*Primary Examiner*—Joseph E. Evans
*Attorney, Agent, or Firm*—John J. Maitner

[57] ABSTRACT

The present invention relates to new phosphonous acid derivatives, especially to α-amino-phosphonous acids and processes for their production. The new phosphonous acids are valuable chemotherapeutica in the treatment of pathogenic bacteria, gram-negative bacteria and yeast.

12 Claims, No Drawings

ALPHA AMINOPHOSPHONOUS ACIDS FOR INHIBITING BACTERIA AND YEAST

The present invention relates to phosphonous acid derivatives, especially to α-amino-phosphonous acids and to processes for their preparation, to medicaments containing the new compounds, and to the use thereof.

According to the invention, there are provided compounds having the general formula I

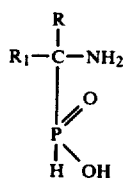

or the corresponding zwitterion form in which R and $R_1$ may be the same or different and can be hydrogen, deuterium, or a lower alkyl group, a lower alkenyl, a lower alkynyl, a cycloalkyl, an aryl group or a 3 to 7-membered heterocyclic ring containing one or more oxygen, nitrogen or sulphur atoms and which may be fused to an aromatic ring, a lower alkyl group substituted by an aryl radical with 6 to 10 carbon atoms, a lower alkyl group substituted by a 3 to 7-membered heterocyclic ring as defined above or R and $R_1$ together form a $C_2-C_7$ polymethylene chain optionally interrupted by an oxygen, nitrogen or sulphur atom and the salts thereof with pharmaceutically acceptable acids or bases and all optical isomers thereof with the proviso that R and $R_1$ may not both be hydrogen.

The term "lower", referred to above and hereinafter in connection with organic radicals or compounds respectively, defines such with up to 6, preferably up to 3, carbon atoms. R and $R_1$ as lower alkyl group may optionally be substituted by one or two $-COOR_2$, $-OR_2$ or $-SR_2$ groups in which $R_2$ is hydrogen or a lower alkyl group with 1 to 3 carbon atoms, $-SS-CH_2-CH-(NH_2)PO_2H_2$ groups, $-NR_3R_4$ groups in which $R_3$ and $R_4$ may be the same or different and can be hydrogen, a lower alkyl group or $R_3$ and $R_4$ together form a polymethylene chain containing up to 6 carbon atoms which may optionally be interrupted by oxygen or nitrogen. R and $R_1$ may also be substituted by

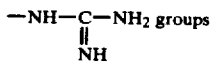

or halogen atoms. Where R and $R_1$ or the substituent of a lower alkyl group is an aryl group or heterocyclic ring it may optionally be substituted by from one to three halogen atoms, $-COOR_5$, $-OR_5$ or $-SR_5$ groups in which $R_5$ is hydrogen or a lower alkyl group with 1 to 3 carbon atoms, methylenedioxy groups, $-NR_3R_4$ in which $R_3$ and $R_4$ may be the same or different and can be hydrogen, a lower alkyl group or $R_3$ and $R_4$ together form a polymethylene chain containing up to 6 carbon atoms which may optionally be interrupted by oxygen or nitrogen or $C_6-C_8$ aryloxy group optionally substituted by $-OH$ or iodine. When R or $R_1$ is a lower alkyl group, this may be a $C_1-C_6$ straight or branched chain alkyl group and may be, for example, a methyl, ethyl, n-propyl, isopropyl, n-butyl, isobutyl, secondary butyl, tertiary butyl, n-amyl, isoamyl or n-hexyl group. When $R_2$ is a lower alkyl group of 1 to 3 carbon atoms this may be a straight or branched chain alkyl group and may be, for example, a methyl, ethyl, n-propyl or isopropyl group.

When R or $R_1$ is a group substituted by a halogen substituent, the halogen may be bromine or iodine but is preferably fluorine or chlorine.

When R or $R_1$ is a lower alkenyl group this may be a $C_2-C_6$ straight or branched chain alkenyl group, and may be, for example, an ethenyl, allyl, crotyl, methallyl, pentenyl or hexenyl group.

When R or $R_1$ represents a lower alkynyl group this may be a $C_2-C_6$ straight or branched chain alkynyl group and may be, for example, an ethynyl, propynyl, butynyl, pentynyl or hexynyl group.

When R or $R_1$ is a cycloalkyl group this may be a cycloalkyl group with 3 to 7 carbon atoms as for example a cyclopropyl, cyclobutyl, cyclopentyl, cyclohexyl or cycloheptyl group.

When R or $R_1$ or the substituent of a lower alkyl group is an aryl group with 6 to 10 carbon atoms, this may be for example a phenyl, tolyl, xylyl, ethylphenyl, propylphenyl, isopropylphenyl, butylphenyl, isobutylphenyl, sec-butylphenyl, tert-butylphenyl or naphthyl group.

When R or $R_1$ or the substituent of a lower alkyl group is a heterocyclic ring containing one or more oxygen, nitrogen or sulphur atoms this may be, for example, aziridine, oxetane, thiophene, furan, pyridine, azepin, isoxazole, thiazole, imidazole, pyrimidine, diazepine, thiadiazole, triazole, triazine, indole or benzofuran.

When R or $R_1$ is a group substituted by a $-COOR_2$ or $-COOR_5$ group the $-COOR_2$ or $-COOR_5$ group may be hydroxycarbonyl, methoxycarbonyl, ethoxycarbonyl, propoxycarbonyl or isopropoxycarbonyl.

When R or $R_1$ is a group substituted by $-OR_2$ or $-OR_5$ the $-OR_2$ or $-OR_5$ group may be hydroxy, methoxy, ethoxy, propoxy or isopropoxy.

When R or $R_1$ is a group substituted by $-SR_2$ or $-SR_5$ the $-SR_2$ or $-SR_5$ group may be thiol, methylthio, ethylthio, propylthio or isopropylthio.

When R or $R_1$ is a group substituted by $-NR_3R_4$, in which the $R_3$ and $R_4$ groups are lower alkyl, these groups may be $C_1-C_3$ straight or branched chain alkyl groups. The $-NR_3R_4$ group including the different meanings enumerated above may be, for example, amino, methylamino, dimethylamino, ethylamino, diethylamino, propylamino, isopropylamino, dipropylamino, diisopropylamino, morpholino or piperidino.

When R and $R_1$ is a group substituted by an aryloxy group with 6 to 8 carbon atoms, the aryloxy group may be phenoxy, tolyloxy, xylyloxy or diiodo-hydroxy phenoxy.

When R or $R_1$ is a lower alkyl group substituted by an aryl group with 6 to 10 carbon atoms or a 3 to 7-membered heterocyclic ring the alkyl group may be a $C_1-C_3$ straight or branched chain alkylene group, for example, $-CH_2-$, $-CH(CH_3)-$, $-(CH_2)_2-$, $-(CH_2)_3-$,

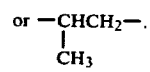

When R and $R_1$ together form a polymethylene chain, this may be for example $-(CH_2)_2-$, $-(CH_2)_3-$, $-(CH_2)_4-$, $-(CH_2)_5-$, $-(CH_2)_6-$, $-(CH_2)_7-$, $-(CH_2)_2CHCH_3(CH_2)_2-$ or $-(CH_2)_2NH(CH_2)_2-$.

Salts of the compounds of formula I are preferably addition salts of the following therapeutically useful inorganic or organic acids or bases:

Examples of acids are hydrochloric, hydrobromic, sulphuric, phosphoric, methanesulphonic, ethanedisulphonic, acetic, trichloroacetic, oxalic, succinic, maleic, fumaric, malic, tartaric, citric and mandelic acids: examples of bases are lithium, sodium, potassium, calcium, magnesium, aluminium, iron, ammonium and substituted ammonium, hydroxides and carbonates, and heterocyclic bases.

The compounds of the invention exhibit valuable pharmacological properties, for example, they are antimicrobial agents, which are effective at low concentrations (0.8 to 50 μg/ml) in inhibiting the growth in vitro of pathogenic bacteria, as for example *Escherichia coli*, *Enterobacter cloacae* and other Enterobacteria, *Pseudomonas aeruginosa* and yeasts, as for example, *candida albicans* and *tropicalis*. The growth of both gram-negative bacteria and yeasts is inhibited.

The new compounds are also effective in vivo. At dose levels between 15–100 mg/kg these compounds given subcutaneously or orally, for example in mice, protect 50% of animals ($ED_{50}$) from death following infections with a lethal dose of pathogenic bacteria as for example *Klebsiella pneumoniae* or *Pseudomonas aeruginosa*.

The new compounds can be administered chemotherapeutically, either alone or in combination with other antimicrobial agents. Another valuable property of the compounds is their synergistic antibacterial activity with other antimicrobial agents for example rifampicin, trimethoprime, D-cycloserin, fluoro-D-alanine and amphotericin B.

The new compounds have low mammal toxicity and can be used for the treatment of diseases in animals, especially mammals, as antiseptic agents, and for the protection of materials from microbial attack.

Particularly useful are compounds of formula I, wherein R and $R_1$ are hydrogen, deuterium, lower alkyl, lower alkenyl, lower alkynyl, or lower alkyl substituted by aryl or heterocyclic groups optionally substituted by from one to three hydroxy or lower alkoxy groups or the salts thereof with pharmaceutically acceptable acids or bases, and all optical isomers thereof, with the proviso that R and $R_1$ may not both be hydrogen.

Preferred are compounds of formula I, wherein R and $R_1$ are hydrogen, deuterium, methyl, ethyl, n-propyl or isopropyl, n-butyl, isobutyl, secondary butyl, tertiary butyl or benzyl groups optionally substituted by one to three hydroxy or lower alkoxy groups or the salts thereof with pharmaceutically acceptable acids or bases, and all optical isomers thereof, with the proviso that R and $R_1$ may not both be hydrogen.

Outstanding are compounds of formula I, wherein R is methyl or isopropyl and $R_1$ is hydrogen or deuterium or the salts thereof with pharmaceutically acceptable acids or bases and all optical isomers thereof.

Especially valuable and suitable for said utility are compounds of formula I wherein R is methyl, isopropyl and $R_1$ is hydrogen or the salts thereof with pharmaceutically acceptable acids or bases and all optical isomers thereof.

Most preferred are the compounds of formula I as listed in the following examples.

One method of preparing the compounds of the general formula I comprises reacting a Schiff's base having the general formula II,

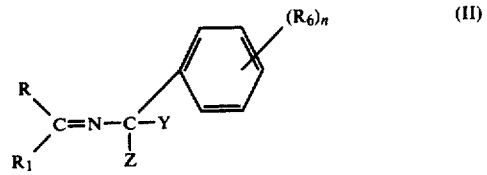

wherein R and $R_1$ have their previous significance and Y is hydrogen, methyl or an aromatic grouping of the formula III

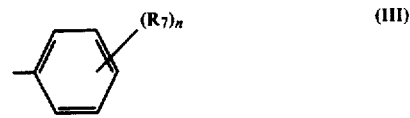

and Z is hydrogen, methyl or an aromatic grouping of the formula IV

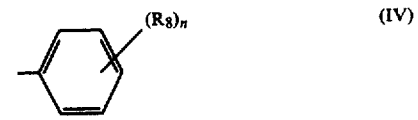

$R_6$, $R_7$ and $R_8$ may be the same or different and may be halogen as for example chlorine or bromine, or a lower alkyl or alkoxy grouping with 1 to 3 carbon atoms and n can be 0, 1 or 2, with hypophosphorous acid to give the N-substituted aminophosphonous acid having the general formula V

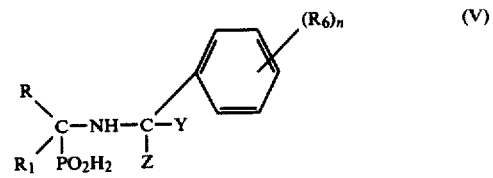

wherein R, $R_1$, Y, Z, $R_6$ and n have their previous significance followed by acid cleavage to produce the acid addition salt of the compound of formula I and subsequent removal of the strong acid. The acid cleavage my be carried out optionally in the presence of compounds which readily react with carbonium ions.

Any protecting groups in R, $R_1$ may be removed at any convenient stage before, during or after reaction with the strong acid.

Preferably n is 0, but when n is 1, or 2, $R_6$, $R_7$ and $R_8$ are preferably the same.

Compounds of general formula V except where Z is hydrogen are new and prepared as described above.

Examples of suitable strong acids are hydrobromic acid, trifluoroacetic acid and formic acid. An example of a compound which reacts readily with carbonium ions is anisole. The compounds of formula I may be liberated by any standard method which facilitates isolation of common amino acids, such as ion-exchange or treatment with propylene oxide.

The Schiff's base having the general formula II may be prepared by the condensation of a suitable aldehyde or ketone having the general formula VI,

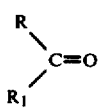

(VI)

wherein R and R₁ have their previous significance with an amine having the general formula VII,

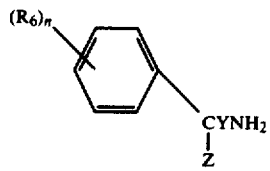

(VII)

wherein Y, Z, R₆ and n have their previous significance.

Another method of preparing the compounds of general formula I comprises reacting a suitable aldehyde or ketone having the general formula VI with the hypophosphorous acid salt of the amine having the general formula VIII,

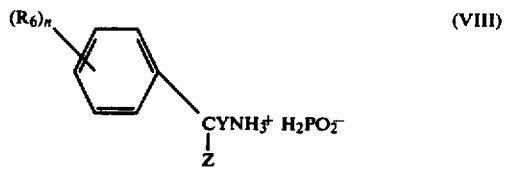

(VIII)

wherein Y, Z, R₆ and n have their previous significance to give the N-substituted α-aminophosphonous acid of general formula V. The compound of formula I is obtained as in the previous method by acid cleavage of the compound of formula V followed by removal of the acid.

Compounds of general formula VIII are new and have not been described before.

A third method of preparing a compound of formula I in which R₁ is hydrogen and R is an aromatic grouping comprises treating an aromatic aldehyde with ammonium hypophosphite to give the α-amino-phosphonous acid of general formula I directly according to the following equation.

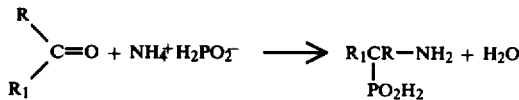

When R₁ is not the same as R the compounds have at least one optical centre and it is to be understood that all optical isomers are covered. The racemic mixtures produced may, if desired, be resolved by conventional methods, with or without prior protection of the amino or phosphonous acid group.

Racemate mixtures can be separated into the pure racemates on the basis of the physico-chemical differences of the constituents, in a known manner, for example by chromatography and/or fractional crystallisation.

Pure racemates can be resolved into the diastereomers according to known methods, for example by recrystallisation from an optionally active solvent, with the aid of microorganisms or by reaction with an optically active acid or base which forms salts with the racemic compound and separation of the salts obtained in this manner, for example on the basis of their different solubilities, and from the diastereomers the antipodes can be liberated by the action of suitable agents. Particularly customary optically active acids are, for example, D- and L-forms of tartaric acid, di-o-toluyl-tartaric acid, malic acid, mandelic acid, camphor-10-sulphonic or quinine acid. Particularly customary optically active bases are, for example, D- and L-forms of α-methylbenzylamine, brucine, ephedrine and cinchonine. Resulting salts may be converted into other salts or into the free and optically active acids or bases, and an optically active acid or base may be converted into an acid or base addition salt by the methods referred to above.

When R or R₁ is deuterium, this may be introduced additionally by deuteration of a compound of formula I where R or R₁ is hydrogen by procedures known to those skilled in the art.

Accordingly, the invention also provides a therapeutic composition comprising an antimicrobially effective proportion of a compound of formula I and a pharmacologically acceptable solid carrier or liquid diluent.

The pharmaceutical compositions according to the invention contain at least one compound of the general formula I as active substance together with a conventional pharmaceutical carrier. The type of carrier actually used depends to a great extent on the intended application; for external use, for example in disinfecting healthy skin, disinfecting wounds and in treating dermatoses and affections of the mucous membranes caused by bacteria, ointments, powders and tinctures are used in particular. The ointment bases may be anhydrous, for instance they can consist of mixtures of wool fat and soft paraffin, or they can consist of aqueous emulsions in which the active substance is suspended. Suitable carriers for powders are, for instance, rice starch and other starches; the bulk weight of the carriers may be made lighter, if desired, for example by adding highly dispersed silicic acid, or may be made heavier by adding talcum. The tinctures may contain at least one active ingredient of the formula I in aqueous ethanol, in particular 45% to 75% ethanol, to which 10% to 20% of glycerol may be added, if desired. Solutions prepared from polyethylene glycol and other conventional solubility promoters, and also, optionally from emulsifying agents, may be used with particular advantage in disinfecting healthy skin. The content of active ingredient in pharmaceutical compositions for external application is preferably in the range of from 0.1% to 5%.

Gargles or concentrates for their preparation, and tablets for slow dissolution in the mouth, are suitable for the disinfection of the mouth and throat. The former are preferably prepared from alcoholic solutions containing 1% to 5% of active substance to which glycerol or flavourings may be added. Lozenges, that is solid dosage units, preferably have a relatively high content of sugar or similar substances and a relatively low content of active substance, for instance 0.2% to 20% by weight, as well as the usual conventional additives such as binding agents and flavourings.

Solid dosage units, in particular tablets, dragees (sugar coated tablets) and capsules, are convenient for use in intestinal disinfection. These units preferably contain from 10% to 90% of the compound of the general formula I to enable the administration of daily doses of from 0.1 to 2.5 grams to adults, or of suitably reduced doses to children to be made. Tablets and dragee cores are produced by combining the compounds of the general formula I with solid, pulverulent carriers such as lactose, saccharose, sorbitol, maize starch, potato starch or amylopectin, cellulose derivatives or gelatines, preferably with the addition of lubricants such as magnesium or calcium stearate or polyethylene glycols of suitable molecular weight. Dragee cores may then be coated, for example with concentrated sugar solutions which can also contain gum arabic, talcum and/or titanium dioxide, or they may be coated with a lacquer dissolved in volatile organic solvents or mixture of solvents. Dyestuffs can be added to these coatings, for instance to differentiate between varying dosages. Soft gelatine capsules and other closed capsules consist, for example, of a mixture of gelatines and glycerol and may contain, for example, mixtures of the compound of formula I with polyethylene glycol. Hard gelatine capsules contain, for example, granulates of an active substance with solid pulverulent carriers, for instance lactose, saccharose, sorbitol mannitol, starches (such as potato starch, maize starch or amylopectin), cellulose derivatives of gelatines, and magnesium stearate or stearic acid.

In all forms for administration compounds of the general formula I can be present as sole active ingredients or they can also be combined with other known pharmaceutically active, and especially antibacterial and/or antimycotically or other antimicrobially active substances, for example to broaden the range of application. They can be combined for example, with 5,7-dichloro-2-methyl-8-quinolinol or other derivatives of 8-quinolinol, with sulfamerazine or sulfafurazole or other derivatives of sulfanilamide, with chloramphenicol or tetracycline or other antibiotics, with 3,4',5-tribromosalicylanilide or other halogenated salicylanilides, with halogenated carbanilides, with halogenated benzoxazoles or benzoxazolones, with polychlorohydroxydiphenylmethanes, with halogen-dihydroxydiphenyl sulphides, with 4,4'-dichloro-2-hydroxydiphenylether or 2,4,4'-trichloro-2-hydroxydiphenylether or other polyhalogenhydroxydiphenylethers, or with bactericidal quaternary compounds or with certain dithiocarbamic acid derivatives such as tetramethylthiuram disulphide or with nitrofurans. Also, carriers which themselves have favourable pharmacological properties may be used, for instance sulphur as a powder base or zinc stearate as a component of ointment bases.

The invention also provides a method of protecting an organic material susceptible to bacterial or other microbial attack which comprises treating the material with a compound of formula I. The organic material may be a natural or synthetic polymeric material, a proteinaceous or carbohydrate substance, or a natural or synthetic fibre or textile material formed therefrom.

PREPARATION OF TABLETS 100 g of an active substance of formula I are mixed with 60.0 g of maize starch and 35.0 g of lactose, the mixture is moistened with a solution of 5.0 g of gelatine and 3.0 g of glycerol in 70.0 g of water and granulated through a sieve. The granulate is mixed with a mixture of 15.0 g of talcum, 10.0 g of maize starch and 2.0 g of magnesium stearate. The resulting mixture is pressed into 1,000 tablets, each containing 100 mg of active substance. If desired, the tablets can be grooved for better adaption of the dosage.

| Preparation of Dragees Composition | for 1,000 dragees |
|---|---|
| I Effective compound of formula I | 100.0 g |
| Maize starch | 27.0 g |
| Gelatine | 8.0 g |
| II Glycerol | 2.0 g |
| Distilled water q.s. ad 100 ml | |
| Maize starch | 10.0 g |
| III Talcum | 7.0 g |
| Magnesium stearate | 1.0 g |
| | 155.0 g |
| IV White dragee coating | |
| Shellac | 2.0 g |
| Sugar | 50.0 g |
| Talcum | 38.0 g |
| Gum arabic | 7.4 g |
| Colloidal silicon dioxide | 2.2 g |
| Titanium dioxide | 0.4 g |

Composition I is granulated in the heat with composition II through a sieve of 1.2 mm mesh diameter. The dried granulate is mixed with composition III and the resulting mixture is pressed into 1,000 dragée cores. These are then coated with composition IV and dried. The dragées obtained weigh 255.0 mg and contain 100 mg of active substance.

| Preparation of Syrup Composition | for 1 liter |
|---|---|
| Active substance of forumla I | 100.0 g |
| Colloidal solicon dioxide | 13.0 g |
| p-Hydroxybenzoic acid methyl ester | 1.4 g |
| p-Hydroxybenzoic acid propyl ester | 0.6 g |
| Citric acid | 1.0 g |
| Sodium cyclamate | 5.0 g |
| Distilled water | 610.0 g |
| Glycerol | 100.0 g |
| Sodium carboxymethyl cellulose | 4.0 g |
| Sugar | 320.0 g |
| | 1155.0 g |

The active substance and the colloidal silicon dioxide are passed through a sieve of 1.2 mm mesh diameter (I).

The p-hydroxybenzoic acid esters, the citric acid and the sodium cyclamate are dissolved in the given amount of boiling distilled water, the glycerol is then added to this solution (II). The sodium carboxymethyl cellulose and the sugar are thoroughly mixed (III).

Composition III is then added at 75° C. to Solution II under stirring until complete dissolution of III. The viscous, slightly turbid liquid is cooled to room temperature, filtered, if necessary, and mixed with composition I. Water is added to the resulting mixture up to the prescribed weight of 1,155.0 g and the syrup obtained is homogenized.

Some examples will now begin, all parts and percentages being by weight unless otherwise stated. The temperatures are given in centigrade.

EXAMPLE 1

(A) 14.4 Parts of isobutyraldehyde was added to 36.6 parts of benzhydrylamine in 100 parts of dry benzene at room temperature with stirring. The cloudy mixture was heated to reflux with water-separation for 4 hours. On cooling the solution was filtered to remove a small amount of solid and evaporated to give isobutylidenebenzhydrylamine.

(B) Hypophosphorous acid (100%, 15.8 parts) dissolved in absolute ethanol was added to a stirred solution of 41.3 parts isobutylidenebenzhydrylamine in absolute ethanol. An exothermic reaction occurred. After standing one hour the reaction was filtered and the white solid dried in vacuo. There was obtained DL-1-benzhydrylamino-2-methylpropanephosphonous acid, melting point 191° (dec.).

(C) 25 Parts of DL-1-benzhydrylamino-2-methylpropanephosphonous acid was stirred rapidly in 100 parts of 60% hydrobromic acid solution for 30 minutes then warmed on a steam bath for 45 minutes. After cooling the oily benzhydryl bromide was extracted carefully with ether and the aqueous acid layer evaporated to dryness. The semi-solid residue was dissolved in 40 parts ethanol and 10 parts of propylene oxide added. Filtration gave DL-1-amino-2-methylpropanephosphonous acid melting point 198°-198.5° (dec.).

EXAMPLE 2

(A) 19.8 Parts of isobutyraldehyde and 62.2 parts of benzhydrylammonium hypophosphite were dissolved in 75 parts of ethanol and the mixture was heated at reflux for 3 hours. After cooling the mixture was filtered to give DL-1-benzhydrylamino-2-methyl-propanephosphonous acid of melting point 189°-192°.

(B) 25 Parts of DL-1-benzhydrylamino-2-methylpropanephosphonous acid was stirred in 100 parts of 60% hydrobromic acid for 30 minutes then warmed on a steam bath for 45 minutes. After cooling the oily benzhydryl bromide was extracted carefully with ether and the aqueous acid layer evaporated to dryness. The semi-solid residue was taken up in 40 parts of ethanol and 10 parts propylene oxide added. Filtration gave DL-1-amino-2-methylpropanephosphonous acid, melting point 201°-201.5° (dec.).

EXAMPLE 3

(A) The procedure described in Example 1A was repeated using 2-methylbutyraldehyde as starting material instead of isobutyraldehyde to give a quantitative yield of 2-methyl-butylidenebenzhydrylamine.

(B) The procedure described in Example 1B was repeated using 2-methyl-butylidenebenzhydrylamine as starting material instead of isobutylidenebenzhydrylamine to give benzhydrylamino-2-methylbutanephosphonous acid of melting point 174°-176°.

(C) The procedure described in Example 1C was repeated using DL-1-benzhydrylamino-2-methylbutanephosphonous acid as starting material instead of DL-1-benzhydrylamino-2-methylpropanephosphonous acid to give DL-1-amino-2-methylbutanephosphonous acid of melting point 203° (dec.).

EXAMPLE 4

(A) The procedure described in Example 1A was repeated using 3-methylbutyraldehyde as starting material instead of isobutyraldehyde to give 3-methylbutylidenebenzhydrylamine.

(B) The procedure described in Example 1B was repeated using 3-methylbutylidenebenzhydrylamine as starting material instead of isobutylidenebenzhydrylamine to give DL-1-benzhydrylamino-3-methylbutanephosphonous acid of melting point 220°.

(C) The procedure described in Example 1C was repeated using DL-1-benzhydrylamino-3-methylbutanephosphonous acid as starting material instead of DL-1-benzhydrylamino-2-methylpropanephosphonous acid to give DL-1-amino-3-methyl-butanephosphonous acid of melting point 222° (dec.).

EXAMPLE 5

(A) The procedure described in Example 1A was repeated using n-heptaldehyde as starting material instead of isobutyraldehyde to give heptylidenebenzhydrylamine.

(B) The procedure described in Example 1B was repeated using heptylidenebenzhydrylamine as starting material instead of isobutylidenebenzhydrylamine to give DL-1-benzhydrylaminoheptanephosphonous acid of melting point 201°-203°.

(C) The procedure described in Example 1C was repeated using DL-1-benzhydrylaminoheptanephosphonous acid as starting material instead of DL-1-benzhydrylamino-2-methylpropanephosphonous acid to give DL-1-amino-n-heptanephosphonous acid of melting point 208°-210° (dec.).

EXAMPLE 6

(A) The procedure described in Example 1A was repeated using benzaldehyde as starting material instead of isobutyraldehyde to give benzylidenebenzhydrylamine of melting point 99°-101°.

(B) The procedure described in Example 1B was repeated using benzylidenebenzhydrylamine as starting material instead of isobutylidenebenzhydrylamine to give DL-1-benzhydrylaminophenylmethanephosphonous acid of melting point 202°-204°.

(C) The procedure described in Example 1C was repeated using DL-1-benzhydrylaminobenzylphosphonous acid as starting material instead of DL-1-benzhydrylamino-2-methylpropanephosphonous acid to give DL-1-aminophenylmethanephosphonous acid of melting point 239°-240° (dec.).

EXAMPLE 7

(A) The procedure described in Example 1A was repeated using p-chlorobenzaldehyde as starting material instead of isobutyraldehyde to give p-chlorobenzylidenebenzhydrylamine of melting point 83°-84°.

(B) The procedure described in Example 1B was repeated using p-chlorobenzylidenebenzhydrylamine as starting material instead of isobutylidenebenzhydrylamine to give DL-1-benzhydrylamino-p-chlorophenylmethanephosphonous acid of melting point 221°-222°.

(C) The procedure described in Example 1C was repeated using DL-1-benzhydrylamino-p-chlorobenzylphosphonous acid as starting material instead of DL-1-benzhydrylamino-2-methylpropanephosphonous acid to give DL-1-amino-p-chlorophenylmethanephosphonous acid of melting point 228°-230° (dec.).

EXAMPLE 8

(A) The procedure described in Example 1A was repeated using acetone as starting material instead of isobutyraldehyde to give methylethylidenebenzhydrylamine.

(B) The procedure described in Example 1B was repeated using methylethylidenebenzhydrylamine as starting material instead of isobutylidenebenzhydrylamine to give 1-benzhydrylamino-1-methylethanephosphonous acid of melting point 207°-210°.

(C) The procedure described in Example 1C was repeated using 1-benzhydrylamino-1-methylethanephosphonous acid as starting material instead of DL-1-benzhydrylamino-2-methylpropanephosphonous acid to give 1-amino-1-methylethanephosphonous acid of melting point 242° (dec.).

EXAMPLE 9

(A) The procedure described in Example 1A was repeated using cyclopentanone as starting material instead of isobutyraldehyde to give cyclopentylidenebenzhydrylamine of melting point 96°–100°.

(B) The procedure described in Example 1B was repeated using cyclopentylidenebenzhydrylamine as starting material instead of isobutylidenebenzhydrylamine to give 1-benzhydrylaminocyclopentane phosphonous acid of melting point 204°–205°.

(C) The procedure described in Example 1C was repeated using 1-benzhydrylaminocyclopentanephosphonous acid as starting material instead of DL-1-benzhydrylamino-2-methylpropanephosphonous acid to give 1-amino-cyclopentanephosphonous acid of melting point 223°–225°.

EXAMPLE 10

(A) The procedure described in Example 1A was repeated using cyclohexanone as starting material instead of isobutraldehyde to give cyclohexylidenebenzhydrylamine of melting point 71°–72°.

(B) The procedure described in Example 1B was repeated using cyclohexylidenebenzhydrylamine as starting material instead of isobutylidenebenzhydrylamine to give 1-benzhydrylaminocyclohexanephosphonous acid of melting point 194°–196°.

(C) The procedure described in Example 1C was repeated using 1-benzhydrylaminocyclohexanephosphonous acid as starting material instead of DL-1-benzhydrylamino-2-methylpropanephosphonous acid to give 1-aminocyclohexanephosphonous acid of melting point 228°–229° (dec.).

EXAMPLE 11

(A) The procedure described in Example 2A was repeated using n-butyraldehyde as starting material instead of isobutyraldehyde to give DL-1-benzhydrylaminobutanephosphonous acid of melting point 215°–216°.

(B) The procedure described in Example 2B was repeated using DL-1-benzhydrylaminobutanephosphonous acid as starting material instead of DL-1-benzhydrylamino-2-methylphosphonous acid to give DL-1-amino-n-butanephosphonous acid of melting point 236°–236.5° (dec.).

EXAMPLE 12

(A) The procedure described in Example 2A was repeated using valeraldehyde to give DL-1-benzhydrylaminopentanephosphonous acid of melting point 209°–210°.

(B) The procedure described in Example 2B was repeated using DL-1-benzhydrylaminopentanephosphonous acid as starting material instead of DL-1-benzhydrylamino-2-methylphosphonous acid to give DL-1-amino-n-pentanephosphonous acid of melting point 230°–232° (dec.).

EXAMPLE 13

(A) The procedure described in Example 2A was repeated using 2-methylbutyraldehyde as starting material instead of isobutyraldehyde to give DL-1-benzhydrylamino-2-methylbutanephosphonous acid of melting point 172°–175°.

(B) The procedure described in Example 2B was repeated using DL-1-benzhydrylamino-2-methylbutanephosphonous acid as starting material instead of DL-1-benzhydrylamino-2-methylphosphonous acid to give DL-1-amino-2-methylbutanephosphonous acid of melting point 203°–205° (dec.).

EXAMPLE 14

(A) The procedure described in Example 2A was repeated using 3-methylbutyraldehyde as starting material instead of isobutyraldehyde to give DL-1-benzhydrylamino-3-methylbutanephosphonous acid of melting point 242°–245°.

(B) The procedure described in Example 2B was repeated using DL-1-benzhydrylamino-2-methylphosphonous acid as starting material instead of DL-1-benzhydrylamino-2-methylphosphonous acid to give DL-1-amino-3-methylbutanephosphonous acid of melting point 222°–223° (dec.).

EXAMPLE 15

0.5 Parts of freshly distilled acetaldehyde was added to a suspension of 2.5 parts of benzhydrylammonium hypophosphite in 10 parts of dioxan at room temperature and the mixture stirred for 15 minutes. The mixture was then heated slowly to 50° when solution occurred and a flocculent precipitate immediately formed. The mixture was allowed to cool to room temperature with vigorous stirring and the orange yellow solid filtered off washed with dioxan and ether and finally with a little cold ethanol to give DL-1-benzhydrylaminoethane phosphonous acid, melting point 220°–221°.

7.2 Parts of 1-benzhydrylaminoethanephosphonous acid was stirred rapidly in 70 parts of 60% hydrobromic acid for 30 minutes then warmed on a steam bath for 45 minutes. After cooling the oily benzhydrylbromide was extracted carefully with ether and the aqueous acid layer evaporated to dryness. The semi-solid residue was taken up in 70 parts of ethanol and 5 parts of propylene oxide added. Filtration gave DL-1-aminoethanephosphonous acid, melting point 223°–224° (dec.).

EXAMPLE 16

A mixture of 13.6 parts anisaldehyde and 8.3 parts ammonium hypophosphite in 100 parts xylene was refluxed with water separation. The xylene was cooled, decanted and the residue boiled with ethanol to give a white solid. Filtration gave DL-1-amino-p-methoxyphenylmethanephosphonous acid, melting point 239°–241° (dec.).

EXAMPLE 17

(A) 5.8 Parts of freshly distilled 3-carbomethoxypropionaldehyde in 10 parts of sodium-dried dioxan was added to a suspension of 12.4 parts benzhydrylammonium hypophosphite in 60 parts of sodium-dried dioxan at 100° and under nitrogen over 15 minutes. 40 Parts water/dioxan was removed by distillation during the addition such that the temperature remained at 100° or above. The resulting clear solution was cooled and diluted with an equal volume of alcohol to give DL-1-benzhydrylamino-3-carbomethoxypropanephosphonous acid, melting point 162°–164°.

(B) 5 Parts of D,L-1-benzyhydrylamino-3-carbomethoxypropanephosphonous acid was stirred rapidly in 50 parts of 60% hydrobromic acid at 80° for 4 hours. After cooling the oily benzhydryl bromide was extracted with ether and the aqueous portion was evaporated to dryness. The solid residue was dissolved in 10 parts of ice cold methanol and 5 parts of propylene oxide was added to give D,L-1-amino-3-carboxypropanephosphonous acid, melting point 162°.

A sample of the solid residue was refluxed with isopropanol for 4 hours. After cooling the mixture was treated with propylene oxide until precipitation was complete to give DL-1-amino-3-carboisopropoxypropanephosphonous acid, melting point 156°.

EXAMPLE 18

(A) 12 Parts of freshly distilled phenylacetaldehyde in 20 parts of sodium dried dioxan was added to a suspension of 25 parts of benzhydrylammonium hypophosphite in 100 parts of sodium-dried dioxan under reflux and under nitrogen, as in Example 17 above, 60 parts of dioxan/water was removed. 50 parts of alcohol was added and D,L-1-benzhydrylamino-2-phenylethanephosphonous acid, melting point 208° was obtained.

(B) 5 Parts of D,L-1-benzhydrylamino-2-phenylethanephosphonous acid was dissolved in 50 parts of hydrobromic acid and heated to 70° for 1.5 hours. The oily benzhydryl bromide was extracted with ether and the aqueous residue was evaporated to dryness. The solid residue was dissolved in 45 parts of ethanol and 1.5 parts of propylene oxide was added to give D,L-1-amino-2-phenylethanephosphonous acid, melting point 227°–228°.

EXAMPLE 19

(A) 10 Parts of freshly distilled p-methoxyphenylacetaldehyde in 20 parts of sodium-dried dioxan was added to a suspension of 17 parts of benzhydrylammonium hypophosphite in 100 parts of sodium-dried dioxan under reflux and under nitrogen as in Example 17 above. 70 Parts dioxan/water was removed. 125 Parts of alcohol was added and DL-1-benzhydrylamino-2-(4-methoxyphenyl)-ethanephosphonous acid, melting point 199°–202°, was obtained.

(B) 6 Parts of DL-1-benzhydrylamino-2-(4-methoxyphenyl)-ethanephosphonous acid was dissolved in 40 parts of hydrobromic acid and heated to 90° for 2 hours. The oily benzhydryl bromide formed was extracted with ether and the aqueous residue evaporated to dryness. The solid residue (3 parts) was dissolved in 15 parts of ethanol and 3 parts propylene oxide added. On standing DL-1-amino-2-(4-hydroxyphenyl)-ethanephosphonous acid, melting point 235° was obtained.

EXAMPLE 20

The procedure used in Example 19 was repeated using freshly distilled 3,4-dimethoxyphenylacetaldehyde instead of p-methoxyphenylacetaldehyde to give DL-1-benzhydrylamino-2-(3,4-dimethoxyphenyl)-ethanephosphonous acid, melting point 205°. This was treated with hydrobromic acid and propylene oxide to give DL-1-amino-2-(3,4-dihydroxyphenyl)-ethanephosphonous acid, melting point 237°–238°.

EXAMPLE 21

The procedure used in Example 19 was repeated using 3-methylthiopropionaldehyde instead of p-methoxyphenylacetaldehyde to give DL-1-benzhydrylamino-3-methylthiopropanephosphonous acid, melting point 207°–208°. This was treated with hydrobromic acid and propylene oxide to give DL-1-amino-3-methylthiopropanephosphonous acid, melting point 231°.

EXAMPLE 22

The procedure used in Example 19 was repeated using 3-methylbutan-2-one instead of p-methoxyphenylacetaldehyde to give DL-1-benzhydrylamino-1,2-dimethylpropanephosphonous acid, melting point 177°. This was treated with hydrobromic acid followed by propylene oxide to give DL-1-amino-1,2-dimethylpropanephosphonous acid, melting point 211°.

EXAMPLE 23

The procedure used in Example 19 was repeated using 2,4-dichlorobenzaldehyde instead of p-methoxyphenylacetaldehyde to give DL-1-benzhydrylamino-1-(2,4-dichlorophenyl)-methanephosphonous acid, melting point 204°–205°. This was treated with hydrobromic acid followed by propylene oxide to give DL-1-amino-1-(2,4-dichlorophenyl)-methanephosphonous acid, melting point 244°.

EXAMPLE 24

The procedure used in Example 19 was repeated using hexahydrobenzaldehyde instead of p-methoxyphenylacetaldehyde to give DL-1-benzhydrylamino-1-cyclohexylmethanephosphonous acid, melting point 199°. This was treated with hydrobromic acid followed by propylene oxide to give DL-1-amino-1-cyclohexylmethanephosphonous acid, melting point 225°.

EXAMPLE 25

The procedure used in Example 19 was repeated using 2-naphthaldehyde instead of p-methoxyphenylacetaldehyde to give DL-1-benzhydrylamino-1-(2-naphthyl)-methanephosphonous acid, melting point 205°–207°. This was treated with hydrobromic acid followed by propylene oxide to give DL-1-amino-1-(2-naphthyl)-methanephosphonous acid, melting point 237°–239°.

EXAMPLE 26

The procedure used in Example 19 was repeated using p-methylbenzaldehyde instead of p-methoxyphenylacetaldehyde to give DL-1-benzhydrylamino-1-(4-methylphenyl)-methanephosphonous acid, melting point 208°–209°. This was treated with hydrobromic acid followed by propylene oxide to give DL-1-amino-1-(4-methylphenyl)-methanephosphonous acid, melting point 235°.

EXAMPLE 27

1 Part of DL-1-amino-2-methylpropanephosphonous acid was treated with 1 part of sodium hydroxide in 15 parts of distilled water until solution occurred. The mixture was evaporated to dryness and the residue was stirred with absolute alcohol. The solid which was filtered off was the sodium salt of DL-1-amino-2-methylpropanephosphonous acid. It had melting point 231°–233° (dec.).

EXAMPLE 28

DL-1-amino-2-methylpropanephosphonous acid was stirred with an excess of hydrobromic acid for 15 minutes. The mixture was evaporated to dryness and the solid residue was washed with acetone. The solid which was filtered off was the hydrobromide of DL-1-amino-2-methylpropanephosphonous acid. It had melting point 134°–136° (dec.).

EXAMPLE 29

(A) 27.5 Parts of DL-1-amino-2-methylpropanephosphonous acid in 100 parts of water was stirred until solution occurred. The pH of the solution was adjusted to 9.5 with 4N sodium hydroxide and the mixture cooled to 0°. 34 Parts of benzyl chloroformate was added over 1 hour and the mixture stirred for 6 hours maintaining at pH 9.0–9.5 by periodic addition of 4N sodium hydroxide. The mixture was allowed to warm up to room temperature and then washed with ether. The aqueous portion was added slowly to a mixture of 120 parts of water and 80 parts of concentrated hydrochloric acid and 400 parts of ice. The solid which was obtained was dried and recrystallised from ethyl acetate/petroleum ether to give DL-1-carbobenzyloxyamino-2-methylpropanephosphonous acid, melting point 108°–111°.

(B) To 34 parts DL-1-carbobenzyloxyamino-2-methylpropanephosphonous acid in 500 parts of absolute ethanol at reflux was added 15 parts of (+)-α-methylbenzylamine in 75 parts of absolute ethanol. 22 Parts of a 1-carbobenzyloxyamino-2-methylpropanephosphonous acid (+)-α-methylbenzylamine salt which had specific rotation $[\alpha]_D^{25} -9.5°$ and melting point 163°–168° crystallised out. This product was recrystallised from absolute ethanol (1 part solid to 15 parts alcohol) to constant melting point and constant specific rotation namely m.p. 169° and $[\alpha]_D^{25} -16.4°$ (DMF/water, 9:1).

(C) (−)-1-carbobenzyloxyamino-2-methylpropanephosphonous acid α-methylbenzylamine salt $[\alpha]_D^{25} -16.4°$ was stirred with an excess of 45% hydrogen bromide in acetic acid at 0° for 1 hour. Propylene oxide was added until precipitation started. Ether was added to complete the precipitation. (−)-1-Amino-2-methylpropanephosphonous acid which had melting point 209° and specific rotation $[\alpha]_D^{25} -3.6°$ (1.5% in water) was obtained.

EXAMPLE 30

(A) The procedure described in Example 29A was repeated to give DL-1-carbobenzyloxyamino-2-methylpropanephosphonous acid.

(B) The procedure described in Example 29B was repeated. The mother liquors obtained from the filtration of the 1-carbobenzyloxyamino-1-methylpropanephosphonous acid α-methylbenzylamine salt of specific rotation $[\alpha]_D^{25} -9.5°$ were evaporated to dryness to give a 1-carbobenzyloxyamino-2-methylpropanephosphonous acid α-methylbenzylamine salt which had a specific rotation $[\alpha]_D^{25} +8°$ and melting point 144°–155°. This product was stirred with an excess of dilute hydrochloric acid to give 1-carbobenzyloxyamino-2-methylpropanephosphonous acid which had a specific rotation $[\alpha]_D^{25} +19°$. This was then treated with (−)-α-methylbenzylamine in the same proportions as described in Example 29B to give a 1-carbobenzyloxyamino-2-methylpropanephosphonous acid α-methylbenzylamine salt which had specific rotation $[\alpha]_D^{25} +13.8°$ and melting point 164°–167°. This product was recrystallised from absolute ethanol (1 part solid to 15 parts alcohol) to constant melting point and constant specific rotation, namely melting point 169° and $[\alpha]_D^{25} +16.2°$ (DMF/water 9:1).

(C) The procedure used in Example 29C was repeated using (+)-1-carbobenzyloxyamino-2-methylpropanephosphonous acid α-methylbenzylamine salt $[\alpha]_D^{25} +16.2°$ instead of the (−)-isomer to give (+)-1-amino-2-methylpropanephosphonous acid $[\alpha]_D^{25} +3.5°$ (1.5% in water), melting point 209°.

EXAMPLE 31

The procedure described in Example 29 (Parts A, B and C) was repeated using DL-1-aminoethanephosphonous acid instead of DL-1-amino-2-methylpropanephosphonous acid to give (−)-1-aminoethanephosphonous acid.

EXAMPLE 32

The procedure described in Example 30 (Parts A, B and C) was repeated using DL-1-aminoethanephosphonous acid instead of DL-1-amino-2-methylpropanephosphonous acid to give (+)-1-aminoethanephosphonous acid.

EXAMPLE 33

(A) The procedure described in Example 1A was repeated using benzylamine (32 parts) in place of benzhydrylamine and isobutyraldehyde (22 parts) to give isobutylidenebenzylamine (49 parts).

(B) The procedure described in Example 1B was repeated using isobutyrylidenebenzylamine (49 parts) in place of isobutylidenebenzhydrylamine to give DL-1-benzylamino-2-methylpropanephosphonous acid, melting point 220° (dec.).

(C) The procedure described in Example 1C was repeated using DL-1-benzylamino-2-methylpropanephosphonous acid in place of DL-1-benzhydrylamino-2-methylpropanephosphonous acid to give DL-1-amino-2-methylpropanephosphonous acid identical to that obtained in Example 1C.

EXAMPLE 34

The procedures described in Example 1A, 1B and 1C was repeated using p,p′-dimethoxybenzhydrylamine instead of benzhydrylamine to give isobutyrylidene-p,p′-dimethoxybenzhydrylamine (cf. 1A), DL-1-(p,p′-dimethoxybenzhydrylamino)-2-methylpropanephosphonous acid (cf. 1B) and DL-1-amino-2-methylpropanephosphonous acid identical with that obtained in Example 1C.

EXAMPLE 35

The procedure described in Example 18 was repeated using p,p′-dimethoxybenzhydrylammonium hypophosphite in place of benzhydrylammonium hypophosphite to give DL-1-amino-2-phenylethanephosphonous acid.

EXAMPLE 36

(A) 7.2 Parts of isobutyraldehyde in 15 parts of sodium-dried dioxan was added to a suspension of 25 parts of benzhydrylammonium hypophosphite in 150 parts of sodium-dried dioxan under reflux. 80 Parts of dioxan was removed and 150 parts of alcohol added. After cooling the mixture was filtered to give DL-1-benzhydrylamino-2-methylpropanephosphonous acid, melting point 189°–192° identical to that obtained in Example 2A.

(B) 5 Parts of DL-1-benzhydrylamino-2-methylpropanephosphonous acid, 5 parts of anisole and 50 parts of trifluoroacetic acid were mixed at room temperature and heated at reflux for 30 minutes. The mixture was cooled and poured into 100 parts of water. The oily layer which formed was extracted with ether and the aqueous layer evaporated to dryness. The resulting white solid was stirred with ethanol and removed by filtration to give DL-1-amino-2-methylpropanephosphonous acid, melting point 201°–202° identical to that obtained in Example 2B.

EXAMPLE 37

(A) The procedure described in Example 36A was repeated using thiophene-2-aldehyde instead of isobutyraldehyde to give DL-1-benzhydrylamino-1-(thien-2-yl)-methanephosphonous acid, melting point 201°.

(B) The procedure described in Example 36B was repeated using DL-1-benzhydrylamino-1-(2-thienyl)-methanephosphonous acid instead of DL-1-benzhydrylamino-2-methylpropanephosphonous acid to give DL-1-amino-1-(thien-2-yl)-methanephosphonous acid, melting point 229°–230°.

EXAMPLE 38

(A) The procedure described in Example 36A was repeated using piperonal (3,4-methylenedioxybenzaldehyde) instead of isobutyraldehyde to give DL-1-benzhydrylamino-1-(3,4-methylenedioxyphenyl)-methanephosphonous acid, melting point 194°–195°.

(B) The procedure described in Example 36B was repeated using DL-1-benzhydrylamino-1-(3,4-methylenedioxyphenyl)-methanephosphonous acid instead of DL-1-benzhydrylamino-2-methylpropanephosphonous acid to give DL-1-amino-1-(3,4-methylenedioxyphenyl)-methanephosphonous acid, melting point 235°–236°.

EXAMPLE 39

(A) The procedure described in Example 36A was repeated using 4-dimethylaminobenzaldehyde instead of isobutyraldehyde to give DL-1-benzhydrylamino-1-(4-dimethylaminophenyl)-methanephosphonous acid, melting point 205°.

(B) The procedure described in Example 36B was repeated using DL-1-benzhydrylamino-1-(4-dimethylaminophenyl)-methanephosphonous acid instead of DL-1-benzhydrylamino-2-methylpropanephosphonous acid to give DL-1-amino-1-(4-dimethylaminophenyl)-methanephosphonous acid, melting point 223°–224°.

EXAMPLE 40

The procedure described in Example 36B was repeated using DL-1-benzhydrylamino-2-methylpropanephosphonous acid and trifluoroacetic acid. It gave DL-1-amino-2-methylpropanephosphonous acid, melting point 201°–202° identical to that obtained in Example 36B.

EXAMPLE 41

The procedure described in Example 36B was repeated using formic acid (99–100%) instead of trifluoroacetic acid. It gave DL-1-amino-2-methylpropanephosphonous acid, melting point 201°–202°, identical to that obtained in Example 36B.

EXAMPLE 42

(A) The procedure used in Example 36A was repeated using 2,4-dihydroxybenzaldehyde instead of isobutyraldehyde to give DL-1-benzhydrylamino-1-(2,4-dihydroxyphenyl)-methanephosphonous acid, melting point 250°.

(B) The procedure described in Example 36B was repeated using DL-1-benzhydrylamino-1-(2,4-dihydroxyphenyl)-methanephosphonous acid instead of DL-1-benzhydrylamino-2-methylpropanephosphonous acid to give DL-1-amino-1-(2,4-dihydroxyphenyl)-methanephosphonous acid.

EXAMPLE 43

(A) The procedure used in Example 36A was repeated using p-acetamidobenzaldehyde instead of isobutyraldehyde to give DL-1-benzhydrylamino-1-(4-acetamidophenyl)-methanephosphonous acid, melting point 196°–200°.

(B) The procedure described in Example 36B was repeated using DL-1-benzhydrylamino-1-(4-acetamidophenyl)-methanephosphonous acid instead of DL-1-benzhydrylamino-2-methylpropanephosphonous acid to give DL-1-amino-1-(4-acetamidophenyl)-methanephosphonous acid. This was treated with dilute hydrobromic acid at reflux followed by propylene oxide to give DL-1-amino-1-(4-aminophenyl)-methanephosphonous acid.

EXAMPLE 44

(A) The procedure used in Example 36A was repeated using pyridyl-3-aldehyde instead of isobutyraldehyde to give DL-1-benzhydrylamino-1-pyrid-3-ylmethanephosphonous acid, melting point 129°–132°.

(B) The procedure used in Example 36B was repeated using DL-1-benzhydrylamino-1-pyrid-3-ylmethanephosphonous acid instead of DL-1-benzhydrylamino-2-methylpropanephosphonous acid to give DL-1-amino-1-(pyrid-3-yl)-methanephosphonous acid-monotrifluoroacetate.

EXAMPLE 45

The procedure described in Example 36B was repeated using DL-1-benzhydrylamino-2-(3,4-dimethoxyphenyl)-ethanephosphonous acid (as obtained in Example 20) instead of DL-1-benzhydrylamino-2-methylpropanephosphonous acid to give DL-1-amino-2-(3,4-dimethoxyphenyl)-ethanephosphonous acid. This was treated with 60% hydrogen bromide at 80° followed by propylene oxide to give DL-1-amino-2-(3,4-dihydroxyphenyl)-ethanephosphonous acid, melting point 237°–238°, identical to that obtained in Example 20.

EXAMPLE 46

The procedure used in Example 19 was repeated using hexene-2-one (allylacetone) instead of p-methoxyphenylacetaldehyde to give DL-1-benzhydrylamino-1-methylpent-4-enephosphonous acid, meltling point 180°. This was treated with hydrobromic acid followed by propylene oxide to give DL-1-amino-1-methyl-4-bromopentanephosphonous acid, melting point 146°–148°.

EXAMPLE 47

(A) The procedure described in Example 36A was repeated using acetaldehyde instead of isobutyraldehyde to give DL-1-benzhydrylaminoethanephosphonous acid, identical to that obtained in Example 15.

(B) The procedure described in Example 36B was repeated using DL-1-benzhydrylaminoethanephosphonous acid instead of DL-1-benzhydrylamino-2- methylpropanephosphonous acid to give DL-1-aminoethanephosphonous acid, identical to that obtained in Example 15.

EXAMPLE 48

(A) The procedure described in Example 36A was repeated using furfuraldehyde instead of isobutyraldehyde to give DL-1-benzhydrylamino-1-(fur-2-yl)-methanephosphonous acid, melting point 193°.

(B) The procedure described in Example 36B was repeated using DL-1-benzhydrylamino-1-(fur-2-yl)-methanephosphonous acid instead of DL-1-benzhydrylamino-2-methylpropanephosphonous acid to give DL-1-amino-1-(fur-2-yl)-methanephosphonous acid, melting point 221°.

EXAMPLE 49

(A) The procedure described in Example 36A was repeated using indol-3-ylacetaldehyde instead of isobutyraldehyde to give DL-1-benzhydrylamino-2-(indol-3-yl)-ethanephosphonous acid.

(B) The procedure described in Example 36B was repeated using DL-1-benzhydrylamino-2-(indol-3-yl)-ethanephosphonous acid instead of DL-1-benzhydrylamino-2-methylpropanephosphonous acid to give DL-1-amino-2-(indol-3-yl)-ethanephosphonous acid.

EXAMPLE 50

(A) The procedure described in Example 36A was carried out using hexene-2-one (allylacetone) instead of isobutyraldehyde to give DL-1-benzhydrylamino-1-methylpent-4-enephosphonous acid, melting point 180°.

(B) The procedure described in Example 36B was repeated using DL-1-benzhydrylamino-1-methylpent-4-enephosphonous acid to give DL-1-amino-1-methylpent-4-enephosphonous acid.

EXAMPLE 51

(A) The procedure described in Example 36A was carried out using cinnamaldehyde instead of isobutyraldehyde to give DL-1-benzhydrylamino-3-phenylprop-2-enephosphonous acid, melting point 202°–203°.

(B) The procedure described in Example 36B was repeated using DL-1-benzhydrylamino-3-phenylprop-2-enephosphonous acid to give DL-1-amino-3-phenylprop-2-enephosphonous acid.

EXAMPLE 52

(A) The procedure described in Example 36A was repeated using indol-3-ylaldehyde instead of isobutyraldehyde to give DL-1-benzhydrylamino-1-(indol-3-yl)-methanephosphonous acid, melting point 154°.

(B) The procedure described in Example 36B was repeated using DL-1-benzhydrylamino-1-(indol-3-yl)-methanephosphonous acid instead of DL-1-benzhydrylamino-2-methylpropanephosphonous acid to give DL-1-amino-1-(indol-3-yl)-methanephosphonous acid.

EXAMPLE 53

(A) The procedure described in Example 36A was carried out using benzyloxyacetaldehyde instead of isobutyraldehyde to give DL-1-benzhydrylamino-2-benzyloxyethanephosphonous acid, melting point 208°–211°.

(B) The procedure described in Example 36B was repeated using DL-1-benzhydrylamino-2-benzyloxyethanephosphonous acid to give DL-1-amino-2-hydroxyethanephosphonous acid.

What is claimed is:

1. A compound of the formula I

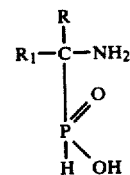

or the corresponding zwitterion form in which R and $R_1$ may be the same or different and can be hydrogen, deuterium, a lower alkyl group, a lower alkyl group substituted by one or two —$COOR_2$, —$OR_2$ or —$SR_2$ groups in which $R_2$ is hydrogen or a lower alkyl group, a lower alkenyl, a lower alkynyl, a cycloalkyl, an aryl group having 6 to 10 carbon atoms, an aryl group substituted by from one to three halogen atoms, —$COOR_5$, —$OR_5$ or —$SR_5$ groups in which $R_5$ is hydrogen or lower alkyl, a lower alkyl group substituted by aryl, or lower alkyl group substituted by aryl having from one to three halogen atoms, —$COOR_5$, —$OR_5$ or —$SR_5$ groups in which $R_5$ is hydrogen or lower alkyl, and the salts thereof with pharmaceutically acceptable acids or bases and optical isomers thereof, with the proviso that R and $R_1$ may not both be hydrogen.

2. A compound as claimed in claim 1 having the general formula I as defined in claim 13, in which R and $R_1$ are hydrogen, deuterium, lower alkyl, lower alkenyl, lower alkynl, lower alkyl substituted by aryl, or lower alkyl substituted by aryl which groups optionally is substituted by from one to three hydroxy or lower alkoxy groups or the salts thereof with pharmaceutically acceptable acids or bases and optical isomers thereof, with the proviso that R and $R_1$ may not both be hydrogen.

3. A compound as claimed in claim 1 having the general formula I as defined in claim 1, wherein R and $R_1$ are hydrogen, deuterium, methyl, ethyl, n-propyl, isopropyl, n-butyl, isobutyl, secondary butyl, tertiary butyl, benzyl, benzyl substituted by one to three hydroxy or lower alkoxy groups or the salts thereof with pharmaceutically acceptable acids or bases all optical isomers thereof, with the proviso that R and $R_1$ may not both be hydrogen.

4. A compound as claimed in claim 1 having the general formula I as defined in claim 1, wherein R is methyl or isopropyl and $R_1$ is hydrogen, deuterium or methyl or the salts thereof with pharmaceutically acceptable acids and bases and all optical isomers thereof.

5. A compound as claimed in claim 1 having the general formula I as defined in claim 1, wherein R is methyl or isopropyl and $R_1$ is hydrogen or the salts thereof with pharmaceutically acceptable acids and bases and all optical isomers thereof.

6. A compound as claimed in claim 1, being the 1-amino-2-methylpropanephosphonous acid or the salts thereof with pharmaceutically acceptable acids and bases.

7. A compound as claimed in claim 1, being the 1-amino-1,2-dimethylpropanephosphonous acid or the salts thereof with pharmaceutically acceptable acids and bases.

8. A compound as claimed in claim 1, being the 1-amino-ethane phosphonous acid or the salts thereof with pharmaceutically acceptable acids and bases.

9. A compound as claimed in claim 1, being the (−)-1-amino-2-methylpropanephosphonous acid.

10. A compound as claimed in claim 1, being the (+)-1-amino-2-methylpropanephosphonous acid.

11. A pharmaceutical composition comprising a pharmaceutically effective amount of a compound as claimed in claim 1, together with a pharmaceutical excipient.

12. A method of treating microbial diseases in a mammal, which consist in administering to said mammal enterally or parenterally a composition as claimed in claim 11.

* * * * *